US 6,560,472 B2

(12) United States Patent
Hill et al.

(10) Patent No.: US 6,560,472 B2
(45) Date of Patent: May 6, 2003

(54) MULTI-CHANNEL STRUCTURALLY ROBUST BRAIN PROBE AND METHOD OF MAKING THE SAME

(75) Inventors: Norman M. Hill, Bothell, WA (US); Andreas N. Hadjicostis, West Linn, OR (US); John W. Swanson, Portland, OR (US)

(73) Assignee: MicroHelix, Inc., Portland, OR (US)

( * ) Notice: Subject to any disclaimer, the term of this patent is extended or adjusted under 35 U.S.C. 154(b) by 21 days.

(21) Appl. No.: 09/886,322

(22) Filed: Jun. 21, 2001

(65) Prior Publication Data
US 2002/0198446 A1 Dec. 26, 2002

(51) Int. Cl.⁷ .............................................. A61B 5/0478
(52) U.S. Cl. ...................................... 600/378; 607/116
(58) Field of Search ........................... 600/378; 607/116

(56) References Cited

U.S. PATENT DOCUMENTS

| | | | | |
|---|---|---|---|---|
| 4,245,645 A | * | 1/1981 | Arseneault et al. | 600/378 |
| 4,461,304 A | * | 7/1984 | Kuperstein | 600/378 |
| 5,524,338 A | * | 6/1996 | Martyniuk et al. | 600/378 |
| 5,843,148 A | | 12/1998 | Gijsbers et al. | 607/116 |
| 5,928,144 A | | 7/1999 | Real | 600/378 |
| 6,052,608 A | * | 4/2000 | Young et al. | 600/378 |
| 6,091,979 A | | 7/2000 | Madsen | 600/377 |
| 6,171,239 B1 | * | 1/2001 | Humphrey | 600/378 |
| 6,301,492 B1 | * | 10/2001 | Zonenshayn | 600/378 |

* cited by examiner

Primary Examiner—Lee Cohen
(74) Attorney, Agent, or Firm—Law Office of Timothy E. Siegel; Timothy E. Siegel

(57) ABSTRACT

A bio-probe having a base and a tip, and comprising a core of substantially rigid, high-strength material, said core tapering inwardly from the base to the tip and a set of conductors extending longitudinally about said core. In addition, dielectric material, substantially electrically isolates each conductor from its surroundings. Also, a set of apertures is defined by the dielectric material to the set of conductors, thereby defining a set of electrodes.

12 Claims, 2 Drawing Sheets

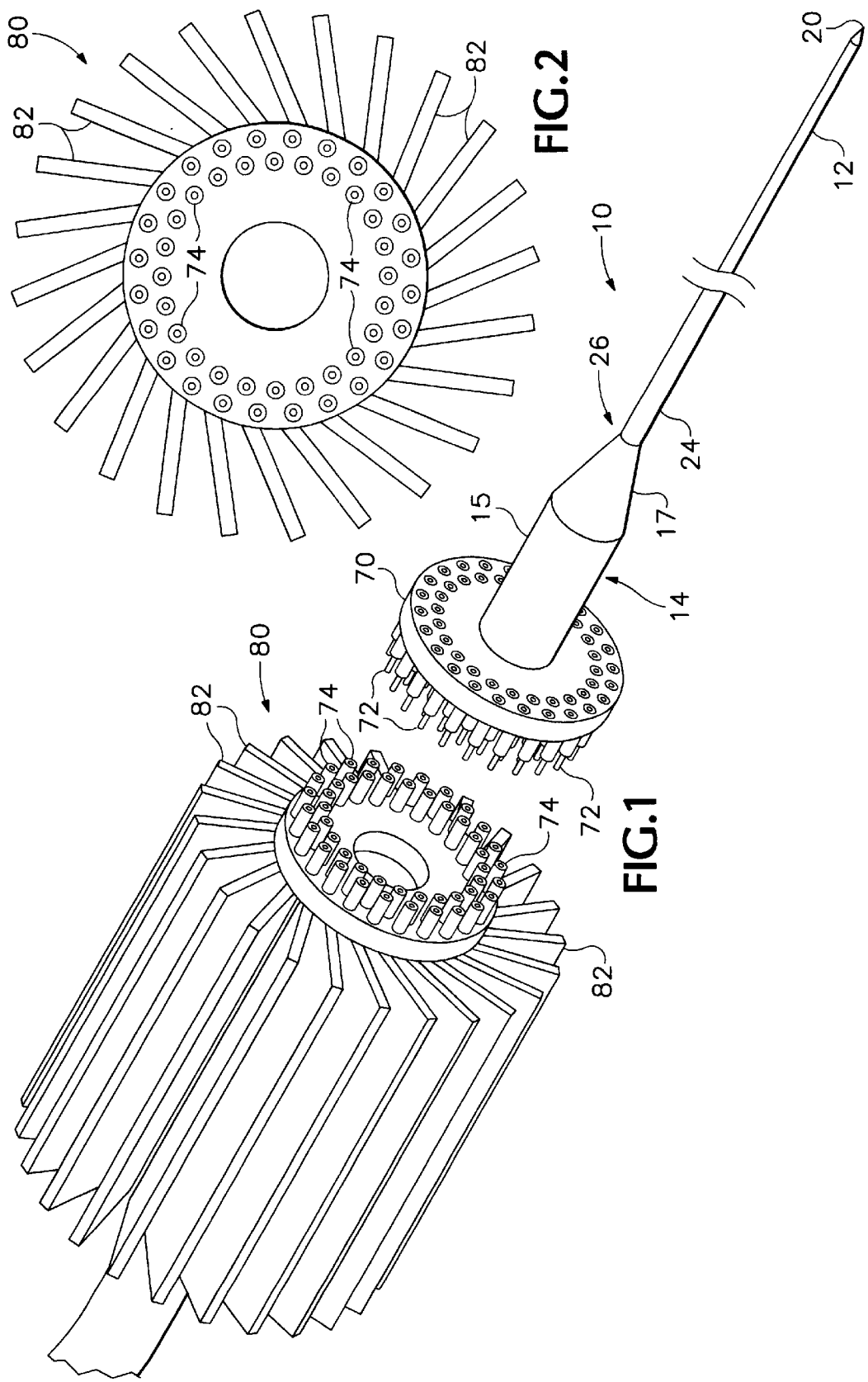

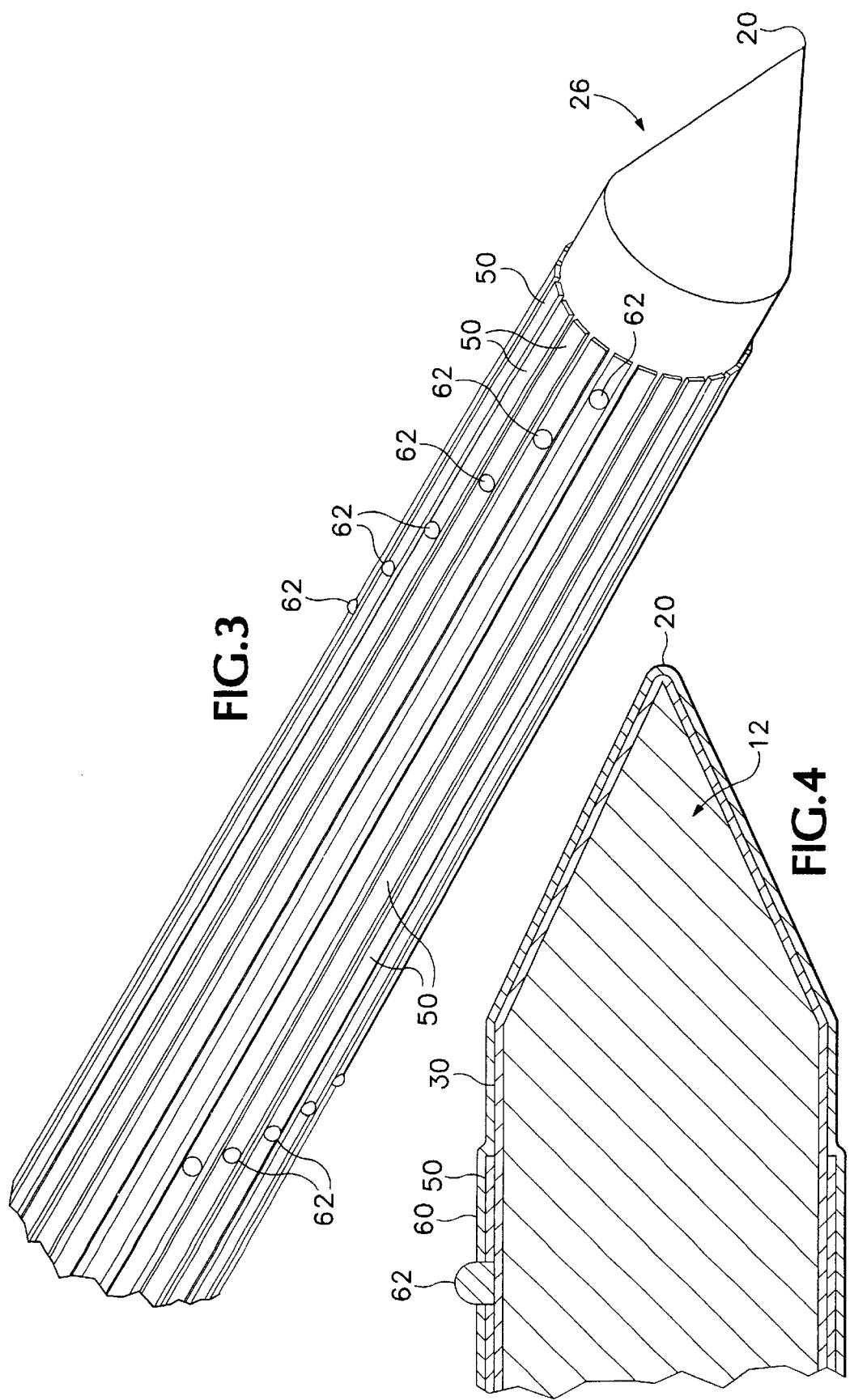

MULTI-CHANNEL STRUCTURALLY ROBUST BRAIN PROBE AND METHOD OF MAKING THE SAME

STATEMENT OF GOVERNMENTAL SUPPORT

This invention was made with government support under grant No. 1R43MH59502-01 awarded by the Small Business Research Program of the Department of Health and Human Services of the Public Health Service. The government has certain rights in the invention.

BACKGROUND OF THE INVENTION

The assembly of a brain probe assembly employed in brain research is quite challenging from both a structural and an electrical standpoint.

Structurally, probes must not fray or in any way come apart when pushed through the dura, a tough membrane covering the brain, and other brain tissue. Probe should have enough strength and rigidity to broach the dura without the need for assistance by, for example, a guide tube or an initial incision.

Moreover, probes must not break, running the risk of leaving a fragment in the brain. Also, they must not cause undue damage to tissue at the sensing site. Inevitably, the tissue separating the sensing site from the brain exterior will suffer some damage as a probe is pushed to its destination.

Electrically, one should note that field signals to be detected in the brain, are typically of the order of 100 to 500 $\mu$volts. The low amplitude of these signals makes it necessary to amplify them as physically close as possible to their source. In fact, the signals involved are so minute that variations in circuit geometry could well affect significantly the detection processing of the signals. It is also highly desirable to minimize cross-talk between any two signals. Given the tight geometries allowable for brain probe design, these requirements are difficult to meet simultaneously.

SUMMARY OF THE INVENTION

In a first separate aspect the present invention is a bio-probe having a base and a tip, and comprising a core of substantially rigid, high-strength material. The core tapers inwardly from the base to the tip and a set of conductors extend longitudinally about the core. In addition, dielectric material, substantially electrically isolates each conductor from its surroundings. Also, a set of apertures are defined by the dielectric material to the set of conductors, thereby defining a set of electrodes.

In a second separate aspect, the present invention is a method of producing a bio-probe. This method includes the step of providing a tapering core of substantially rigid material. The core is then coated with dielectric material and this dielectric material is coated with a first layer of conductive material. The conductive material is then divided into longitudinal traces, extending from the base into proximity to said tip. The conductive material is then coated with a second layer of dielectric material. Finally, portions of the second layer of dielectric material are removed to form apertures to the conductive material, thereby forming electrodes.

In a third separate aspect, the present invention is a bio-probe assembly for measuring bio-electrical signals, comprising, a probe portion having a distal end and a proximal end and a set of electrodes at said distal end for detecting the bio-electrical signals. Each electrode is connected to a longitudinal conductor, extending to the proximal end and a set of substantially identical amplifier circuit cards connected to the longitudinal conductors. Accordingly, each bio-electrical signal is amplified in substantially the same manner.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 1 is an exploded perspective view of bio-probe assembly according to the present invention.

FIG. 2 is a front view of the circuit card assembly of the bio-probe assembly of claim 1.

FIG. 3 is an expanded perspective view of the tip of the bio-probe assembly of FIG. 1.

FIG. 4 is a greatly expanded cross-sectional view of the tip of the bio-probe assembly of FIG. 1.

DETAILED DESCRIPTION OF THE PREFERRED EMBODIMENT

A preferred embodiment of a brain probe assembly 10, according to the present invention is composed of a probe core 12 and a handle core 14. The probe core 12 is made of tungsten, chosen for its material stiffness and tensile strength. Probe core 12 must be absolutely straight. To achieve this end, a straightening machine that pulls on core 12, thereby creating tensile stress and annealing core 12 may be used. A tip or distal end 20 of probe core 12 has a diameter of 200 microns (8.0 mils) and a base or proximal end 24 of core 12 has a diameter of 600 microns (24 mils). In addition, core 12 is 89 mm (3.5") long. The tip 20 is preferably formed by way of centerless grinding. Probe core 12 should be electro polished so that the deposition of materials onto it (see below) can be accomplished efficiently and so that the finished assembly 10 can pass through brain tissue as smoothly as possible.

For ease of assembly and so that operating personnel may more easily handle assembly 10, the handle core 14 is expanded in cross-section relative to probe core 12. Although the handle core 14 is preferably a unitary piece of medical grade 304 stainless steel, it may be conceptually divided into a cylinder 15, having a diameter of 4.826 mm (0.19"), and a frustum 17. The frustum 17 tapers inwardly at 15° angle from the sides of cylinder 15. A 600 $\mu$m (24 mil) aperture (not shown) at the narrow end of frustum 17 permits introduction of the base of probe core 12, after which probe core 12 is joined to handle core 14, by way of an epoxy, to form joint core 26. The epoxy used must be conductive, so that the probe core 12 is grounded to the base core 14, heat resistant, so that it withstands the sterilization process that the probe 10 must undergo in use. It must also be able to withstand the different degrees of expansion that stainless steel and tungsten undergo during the sterilization process. An epoxy that is available from Epoxy Technology, Inc. of Billerica, Mass. under the designation E3084 appears to meet these requirements. In an alternative preferred embodiment, the probe core 12 is laser-welded to the base core 14.

After joint core 26 is produced, it is dip coated with a dielectric epoxy, which has been premixed with a surfactant to promote an even coating, to form an insulating coat 30. The desirable characteristics for an epoxy to be used are biocompatibility, heat tolerance to withstand the sterilization process, low viscosity to produce a thin film, a heat accelerated cure and a high bulk resistivity and a low dielectric coefficient to avoid electrical losses and withstand electrostatic charges. One epoxy that appears to meet these requirements is available as #377 from Epoxy Technology, Inc. of Billerica, Mass. A suitable surfactant is available as FC-430 from 3M of St. Paul, Minn. In an additional preferred embodiment quartz crystal, glass or a similar dielectric material is vacuum deposited to form coat 30. In this preferred embodiment, in order to gain adherence, however, a 200 Å coat of chrome (not shown) is first applied, also through vacuum deposition on core 26 to promote the adhesion of coat 30. The thickness of coat 30 is chosen to minimize the capacitance between core 26 and the conductive traces 50 (see below) deposited over it.

On top of coat 30, a 0.5 $\mu$m thick plate of conductive material (not shown as such but later rendered into a set of traces 50) is, preferably, vacuum deposited. This plate 50 also may be adhered by way of a 200 Å layer of vacuum deposited chrome (not shown). Plating 50 must be highly conductive and, if vacuum coating is used, must be an element of the periodic table. Accordingly, gold, platinum and iridium are among the materials that may be used. Other deposition techniques, such as chemical deposition, may permit the application of other highly conductive materials, such as a conductive polymer. The material used to create plating 50 must also be susceptible to removal by laser ablating or an etching process.

Next, plate 50 is sectioned into 24 longitudinal traces 50 (other numbers of traces 50 are possible) extending from approximately the tip 20 to the proximal end of base core 14. Accordingly, near the tip 20 the traces 50 have a pitch of about 27 $\mu$m, near the base 24 have a pitch of about 80 $\mu$m at the proximal end of handle 14 have a pitch of about 630 $\mu$m. Of particular utility for performing task of sectioning the conductive plate into traces 50 is a frequency multiplied ND:YAG laser, which can cut kerfs to separate the traces on the order of 5–10 $\mu$m width.

In one preferred embodiment there are just four traces 50. Using this embodiment a compound probing device may be built that incorporates an array of probe assemblies 10 to sense and or stimulate a number of neural sites separated not just in depth, but also transversely to probe assembly 10 longitudinal dimension.

Next, the conductive traces 50 are coated with an outer layer 60 of high coefficient dielectric material. An additional dip coat of epoxy #377 is one way of accomplishing this. Another method is a vacuum deposition of glass or quartz crystal placed, again over an intermediate 200 Å layer of chrome. Dielectric layer 60 preferably has a thickness of from 10 to 40 um to avoid damage by static electric discharge. A laser is used to ablate this outer layer to create several apertures extending through layer 60, having a diameter of about 10 $\mu$m at each prospective microelectrode site. A platinum-iridium electrode 62 is built up, preferably by electroplating, at each of these sites.

Base 14 is attached to a plate 70 that includes outwardly extending conductive traces (not shown) that connect traces 50 to a set of connector pins 72. In turn a set of connectors 72 on plate 70 attach to a matching set of connectors 74 on a circuit card assembly 80. Assembly 80 includes a set of 24 circuit cards 82, one for each trace, each bearing an identical amplification circuit for processing each signal from each trace 50 in an identical manner.

The advantages of the present invention should now be apparent. Probe assembly 10 is strong, smooth and sleek, for moving through brain tissue to the site of interest. The cross capacitance between traces 50 is minimized due to the shape of the traces 50, which are curved solid rectangles, on the order of 0.5 $\mu$m thick but varying between 10 $\mu$m and 50 $\mu$m wide. Finally, identical circuits 82 ensure equal treatment for each trace signal.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow.

What is claimed is:

1. A bio-probe having a base and a tip, and comprising:
   (a) a core of substantially rigid, high-strength material, said core being substantially circular in cross-section, and tape ring inwardly from said base to said tip, said tapering being substantially uniform in cross-section so that said tip of said core has substantially the same cross-sectional shape as said base of said core, but is of a smaller cross-sectional size;
   (b) a set of conductors extending longitudinally from said base to a position near to said tip and collectively substantially circumscribing said core;
   (c) dielectric material, substantially electrically isolating each said conductor from its surroundings; and
   (d) a set of apertures through said dielectric material to said set of conductors, hereby defining a set of electrodes.

2. The bio-probe of claim 1, wherein said dielectric material is divided into a first layer of dielectric material and a second layer of dielectric material and wherein said first layer of dielectric material is deposited directly upon said core.

3. The bio-probe of claim 2, wherein said second layer of dielectric material is made of epoxy resin.

4. The bio-probe of claim 2, wherein said set of conductors are made from conductive material that is deposited directly upon said first layer of dielectric material.

5. The bio-probe of claim 4, wherein each conductor of said set of conductors is roughly rectangular in cross section and is each more than three times as wide as it is thick and is substantially conformal over said first layer of dielectric material.

6. The bio-probe of claim 4, wherein each pair of conductors of said set of conductors is mutually separated by a trench running longitudinally along the length of said bio-probe.

7. The bio-probe of claim 1, wherein said core is comprised of tungsten.

8. The bio-probe of claim 1, wherein said apertures are filled with conductive material.

9. The bio-probe of claim 1, wherein said dielectric material has an exterior surface and said apertures are filled with conductive material that extends onto and beyond said exterior surface of said dielectric material.

10. The bio-probe of claim 1, wherein said core, said set of conductors and said dielectric material form a first portion that has a base and further including a second portion having a tip and a base and wherein said tip of said second portion is positively attached to said base of said first portion.

11. The bio-probe of claim 1, wherein said core is smoothly circular in cross-section.

12. The bio-probe of claim 1, wherein said core has quadrilateral symmetry in cross-section.

* * * * *